United States Patent [19]

Carney

[11] Patent Number: 5,112,737
[45] Date of Patent: May 12, 1992

[54] MONOCLONAL ANTIBODIES AGAINST ACTIVATED RAS PROTEINS WITH AMINO ACID MUTATIONS AT POSITION 13 OF THE PROTEIN

[75] Inventor: Walter P. Carney, Brighton, Mass.

[73] Assignee: Applied bioTechnology, Inc., Cambridge, Mass.

[21] Appl. No.: 724,224

[22] Filed: Jul. 1, 1991

Related U.S. Application Data

[62] Division of Ser. No. 158,730, Feb. 22, 1988, Pat. No. 5,028,527.

[51] Int. Cl.$^5$ .................. C12Q 1/00; G01N 33/53; C07K 15/28; C12N 5/20
[52] U.S. Cl. .................. 435/7.92; 530/387.7; 530/387.9; 530/388.85; 435/70.21; 435/172.2; 435/240.27; 435/7.23; 424/85.8; 436/548; 935/104; 935/108; 935/110
[58] Field of Search ............... 530/387, 388; 424/85.8; 435/70.21, 172.2, 240.27, 7.92; 436/519, 536, 548; 935/104, 108, 110

[56] References Cited

U.S. PATENT DOCUMENTS

| | | | |
|---|---|---|---|
| 4,535,058 | 8/1985 | Weinberg et al. | 435/6 |
| 4,568,640 | 2/1986 | Rubin | 435/70.1 |
| 4,659,678 | 4/1987 | Forrest et al. | 436/512 |
| 4,699,877 | 10/1987 | Cline et al. | 435/6 |
| 4,725,550 | 2/1988 | Perucho et al. | 435/320.1 |
| 4,762,706 | 8/1988 | McCormick et al. | 424/85.8 |
| 4,786,718 | 11/1988 | Weinberg et al. | 530/387 |
| 4,820,631 | 4/1989 | Lacal et al. | 435/6 |
| 4,898,932 | 2/1990 | Carney | 530/387 |
| 4,957,859 | 9/1990 | Bizub | 435/7.92 |
| 5,028,527 | 7/1991 | Carney | 435/7.92 |

FOREIGN PATENT DOCUMENTS

0175360 3/1986 European Pat. Off. .
0177814 4/1986 European Pat. Off. .
0203587 12/1986 European Pat. Off. .

OTHER PUBLICATIONS

Bizub et al., "Detection of Transforming ras Proteins Containing Leucine at Position 61 by a New Mouse Monoclonal Antibody", ras(53-69)Leu 61, Cancer Res. 49:6425-6431, 1989.

Capella et al., "C-K-ras Mutations in Colo-Rectal and Pancreatic Tumorigenesis", The Moleculr Basis of Human Cancer Meeting, Abstract, Jun. 1990.

Carney et al., "Monoclonal Antibody Specific for an Activated RAS Protein," *Proc. Natl. Acad. Sci. USA* 83:7485-7489, Oct. 1986.

Bos et al., "Amino Acid Substitutions at Codon 13 of the N-ras Oncogene in Human Acute Myeloid Leukaemia", *Nature* 315:726-730, Jun. 1985.

Hirai et al., "A Point Mutation at Codon 13 of the N-ras Oncogene in Myelodysplastic Syndrome", *Nature* 327:430-432, Jun. 4, 1987.

Nishida et al., "A Point Mutation at Codon 13 of the N-ras Oncogene in a Human Stomach Cancer", *Biochem. Biophys. Res. Comm.* 146:247-252, 1987.

Primary Examiner—Margaret Moskowitz
Assistant Examiner—Robert D. Budens
Attorney, Agent, or Firm—Sewall P. Bronstein; Ronald I. Eisenstein

[57] ABSTRACT

Monoclonal antibodies reactive with oncogenic and activated ras p21 proteins containing aspartic acid or valine at position 13 and unreactive with normal ras p21 proteins containing glycine at position 13. The antibodies are secreted by hybridomas obtained by immunizing mice with synthetic peptides corresponding in amino acid sequence to positions 5–19 or normal ras p21 proteins, except having aspartic acid or valine in place of glycine at position 13 and except for the addition of cysteine at the amino terminal end of the peptide. The antibodies and immunoreactive fragments are useful in the diagnosis, staging and classification of malignant and premalignant lesions.

6 Claims, No Drawings

MONOCLONAL ANTIBODIES AGAINST ACTIVATED RAS PROTEINS WITH AMINO ACID MUTATIONS AT POSITION 13 OF THE PROTEIN

This is a divisional of co-pending application Ser. No. 07/158,730 filed on Feb. 2, 1988, now U.S. Pat. No. 5,028,527.

FIELD OF INVENTION

This invention concerns murine monoclonal antibodies (Mabs) and antibody fragments that are immunoreactive with activated (oncogenic) ras proteins with amino acid substitutions of aspartic acid or valine at position 13 of the ras protein. These activated ras proteins collectively termed p21 have been discovered in diseases such as acute myelogenous leukemia and in preleukemic diseases. termed myelodysplastic syndrome. Also of concern are the hybridoma cell lines that secrete the antibodies, and use of the antibodies or antibody fragments of the invention in the diagnosis, staging and classification of malignant and premalignant lesions.

BACKGROUND OF THE INVENTION

Normal genes (DNA) encode proteins necessary for the growth, differentiation and survival of cells. Overexpression, mutation or expression of normal proteins at an inappropriate time in the cell cycle can transform normal cells to cancer cells. When normal genes act in this manner they are referred to as oncogenes.

Ras genes are found in a wide variety of nucleated mammalian cells and participate in normal cellular functions. The family of ras genes encode a series of immunologically related proteins with a molecular weight of 21,000 and are referred to as p21s. Ras genes present in mammalian cells have been demonstrated to be homologous to murine sarcoma viral oncogenes. (Weinberg, et al., U.S. Pat. No. 4,535,058: Harvey (1964), Nature. 104:1104: Kirsten et al. (1967). J.N.C.I., 38:311). Viral and cellular ras genes encode membrane bound proteins (Willingham, et al. (1980), Cell. 19:1005) which bind quanine nucleotides (Scolnick, et al. (1979) PNAS (USA), 76:5355: Pageorge, et al. (1982), J. Virol., 44:509: and Finek, et al. (1984), Cell. 37:151) and possess intrinsic GTPase activity (McGrath et al. (1984). Nature, 310:644: Sweet et al. (1984). Nature, 311:273; Gibbs et al. (1984) PNAS (USA) 81:5704; and Manne et al. (1985) PNAS 82:376).

DNA mediated transfection experiments using NIH3T3 cells as recipients have led to the identification of a family of activated transforming genes homologous to the ras genes of the Harvey (ras-H) and Kirsten (ras-K) sarcoma viruses. A third member of the ras family designated ras-N has been identified but has not been found to have a retroviral counterpart. Activated ras genes are structurally distinct from their normal homologs, having amino acid substitutions in the protein at positions 12,13 or 61. (Tabin, et al. (1982), Nature, 300:143: Reddy et al. (1982) Nature, 300:149; Bos et al. (1985) Nature, 315:716; and Yuasa et al. (1983) Nature, 303:775-779. Taparowsky et al., Banbury Report, 14:123-133 (1983) cited in Chem. Abstracts, CA 100(1):1425n, teaches that the change at residue 12 from N-terminus of the H ras p21 from glycine to valine is sufficient to convert the normal gene to a transforming gene. Shimizu et al., Nature, 304 (5926), 497-500 (1983) cited in Chem. Abstracts, 99(19):1530936, teaches the presence of a cysteine residue at amino acid 12 in the human lung cancer cell line calu-1 homolog of the v-ki-ras gene. Fasano et al., J. Mol. Appl. Genet., 2(2):173-180 (1983) cited in Chem. Abstracts CA, 99(19):153080v, teaches that the T24H-ras-1 gene product is nearly identical to the v-H-ras p21 transforming protein encoded by Harvey sarcoma virus. Activated ras transforming genes have been found in 10-20% of neoplasms including sarcomas, neuroblastomas, melanomas and carcinomas. In certain forms of leukemia activated ras genes and the corresponding proteins have been found in over 50% of the tumors studied. These activated ras gene and mutated proteins have also been found in established cell lines as well as primary and metastatic tumors. Gambke et al. (Nature 307:476, 1984) demonstrated a transforming N-ras gene in bone marrow cells from a patient with acute myeloblastic leukemia (AML). In contrast DNA from fibroblast cells from the same patient was not transforming.

The p21 ras protein in its normal nonactivated form contains the glycine amino acid at positions 12 and 13 and the glutamine amino acid at position 61. The p21 protein found in normal cells has the following primary amino acid structure for amino acid residues 5 through 19: [5]Lysine-Leucine-Valine-Valine-Valine-Glycine-Alanine-Glycine-Glycine-Valine-Glycine-Lysine-Serine-Alanine-Leucine[19].

Previous reports (Furth et al. (1982), J. Virol., 43:294) have described several rat monoclonal antibodies reactive with normal and activated or oncogenic (mutated) ras p21 proteins in yeast and mammalian cells. Carney et al., Proc. Nat. Acad. Sci., USA, Vol. 83, pp. 7485-7489 (1986) and EPO Publication No. 019003 published on Aug. 6, 1986 disclose a monoclonal antibody specific for an activated ras protein. This monoclonal antibody was raised against a synthetic peptide corresponding to amino acids of a mutated ras gene encoding valine instead of glycine at position 12. Carney et al., UCLA Symp. Mol. Cell. Biol., New Ser. 1985 cited in Chem. Abstracts 104:1665706, disclose a monoclonal antibody raised against a ras related synthetic peptide showing immunoreactivity with human carcinomas. Carney et al. reported a series of monoclonal antibodies raised against synthetic peptides containing amino acid substitutions of glutamic acid, arginine and valine at position 12 (A Book of Abstracts from the 3d Annual Meeting on Oncogenes held at Hood College, Frederick, Md., Jul. 7-11, 1987). Other monoclonal antibodies generated by various methods have also been reported to react with the various forms of the ras p21 protein. Hand et al. Proc. Nat. Acad. Sci. USA, Vol. 81, pp. 5227-5231 (1984); Thor et al., Nature, Vol. 311, pp. 562-565 (1984); Wong et al., Cancer Research, Vol. 46, pp. 6029-6033 (1986), and Tanaka, Proc. Natl. Acad. Sci., USA, Vol. 82, pp 3400-3404 (1985).

Several scientific reports have shown that normal cells contain ras proteins with glycine at position 13.

In 1985 Bos et al. (Nature 315:726 1985) demonstrated that DNA isolated from cells of AML patients were able to transform NIH3T3 cells. This result is indicative and highly suggestive for the presence of an oncogene. These transforming genes were shown to be activated ras genes. In contrast DNA from normal tissues were non-transforming and therefore did not contain activated N ras. These investigators analyzed the activated N ras genes for the presence of mutations using oligonucleotide probe and found that the activated N ras genes contain mutations that result in amino acid substitutions at position 13 of protein. These mutations at position 13 were shown to be either aspartic acid or valine instead of the normal amino acid glycine.

Two reports in 1987 described ras mutations with arginine at position 13. Nitta et al. have shown (Jpn J Cancer Res. (Gann), 78,21–26 1987) an amino acid substitution of arginine for glycine at position 13 of an activated N ras p21 isolated from a human rectal carcinoma. A report by Hirai et al. (Nature 327:430 1987) has shown activated N ras genes in bone marrow cells from patients with myelodysplastic syndrome. The observations made by Hirai et al. suggests that the presence of activated N ras genes with position 13 mutations may be important in early stages of leukemia.

A report by E. Liu et al. (Nature 330:186, 1987) demonstrated the presence of the aspartic acid mutation at position 13 of the ras p21 in a patient with myelodysplastic disease 1.5 years before the patient progressed to acute leukemia. Thus screening patients with myeloplastic syndrome for the presence of activated ras proteins with position 13 mutations with monoclonal antibodies that are the subject of this invention may be a valuable test to predict which patients with myeloplastic syndrome have an increased risk of developing acute leukemia.

Most recently Wodnar-Filipowica et al. reported (Oncogene, pp. 457–461, Vol. 1., No. 4 (1987) the presence of activated N ras genes in a human T cell non-Hodgkin's lymphoma. These studies demonstrated the substitution of cysteine for glycine at position 13.

STATEMENT OF DEPOSIT

1. The hybridoma cell lines which were found to secrete a monoclonal antibody reactive with activated ras proteins containing aspartic acid at position 13 and the subject of this invention were deposited in the American Type Tissue Culture Collection (ATCC) under the Budapest Treaty. Hybridoma D753-13(129) was designated HB 9632 and hybridoma D765-13 (146) was designated HB 9633.

2. The hybridoma cell line which was found to secrete a monoclonal antibody reactive with activated ras proteins containing valine at position 13 and the subject of this invention was deposited in the American Type Tissue Culture Collection (ATCC) under the Budapest Treaty. Hybridoma V647-13 was designated HB 9634.

SUMMARY OF THE INVENTION

The subject of this invention is the induction, production and characterization of monoclonal antibodies that react with the activated ras protein containing aspartic acid or valine amino acid at position 13 and these monoclonal antibodies do not react with the normal ras protein containing glycine at position 13. Antibodies described in this invention are valuable diagnostic tools for the detection of activated p21 s in neoplastic and preneoplastic cells. Antibodies described in this invention are valuable tools for determining whether cells from acute myelogenous leukemia patients or patients with preleukemic syndromes have activated ras p21 s with either aspartic acid or valine at position 13.

Balb/c X C57B1/6 mice were immunized on several occasions with synthetic peptides designated peptide 1 or peptide 2. Peptide 1 has the amino acid structure of an activated p21 with aspartic acid at position 13 of p21 whereas peptide 2 has the amino acid structure of an activated p21 with valine at position 13. Both peptides 1 and 2 were synthesized with a cysteine amino acid at the amino terminal end of the peptide. Although a cysteine amino acid does not occupy the position immediately preceding lysine which occupies position 5 of the ras protein, cysteine was added to facilitate coupling of the peptides to carrier proteins. However, coupling via cysteine was not used because the procedure was too cumbersome. Cysteine was not removed from the fragments synthesized and did not interfere with identifying the appropriate hybridoma cell lines that secrete the antibodies or antibody fragments of interest. Peptide 1 has the following structure: Cysteine-Lysine-Leucine-Valine-Valine-Valine-Glycine-Alanine-Glycine-Aspartic Acid-Valine-Glycine-Lysine-Serine-Alanine-Leucine. Peptide 2 has the following structure: Cysteine-Lysine-Leucine-Valine-Valine-Valine-Glycine-Alanine-Glycine-Valine-Valine-Glycine-Lysine-Serine-Alanine-Leucine.

Peptides 1 and 2 were coupled to carrier proteins Bovine Thyroglobulin (BTG) or Keyhole Limpet Hemocyanin (KLH) using glutaraldehyde and inoculated into mice. Spleen cells from the mice immunized with either peptide 1 or 2 coupled to BTG or KLH were fused with Sp2/O mouse myeloma cells and two weeks later culture supernatants from hybridomas were screened by enzyme-linked immunosorbent assay (ELISA). Hybridomas designated D753-13(129) and D765-13(146) were selected because of their reactivity on the immunizing peptide 1 (containing aspartic acid at position 13) and because of their lack of reactivity with peptide 2 (valine at position 13) or a third peptide designated peptide 3. Peptide 3 differed from peptides 1 and 2 by the fact that it has the normal amino acid glycine at position 13 instead of the aspartic acid or valine substitutions at position 13. The structure of peptide 3 is Cysteine-[5]Lysine-Leucine-Valine-Valine-Valine-Glycine-alanine-Glycine-Glycine-Valine-Glycine-Lysine-Serine-Alanine-Leucine[19]. Hybridoma designated V647-13 was selected because of its reactivity with peptide 2 (valine at position 13) and because of the lack of reactivity with peptide 1 (aspartic acid at position 13) and peptide 3 (glycine at position 13).

DETAILED DESCRIPTION OF THE INVENTION

Immunizations

Balb/c×C57BL/6 mice were immunized with an immunogen designated ASPKLH. This immunogen was composed of peptide 1 (containing the aspartic acid substitution at position 13) coupled to the carrier protein Keyhole Limpet Hemocyanin. The peptide was attached to a carrier protein prior to injection into mice in order to enhance the immunogenicity of the peptide. The first inoculation of Asp/KLH was given in complete Freunds Adjuvant on day 1 and subsequent inoculations of 500 μg of immunogen were given at two week intervals until fusion. Three days before fusion mouse #4341 from which D753-13 was derived and mouse #4355 from which D765-13 was derived were given an intraperitoneal boost of the appropriate immunogen ASP/KLH immunogen.

Balb/c×C57BL/6 mice were immunized with an immunogen designated Val/KLH. This was composed of peptide 2 (containing the valine amino acid at position 13) coupled to the KLH carrier protein. As with the mice described above the first inoculation consisted of the immunogen mixed with Complete Freunds Adjuvant and subsequent inoculations of 500 μg of immunogen were given at two week intervals until fusion. Three days prior to fusion mice were given an i.p. boost of the Val/KLH immunogen.

HYBRIDOMA METHODOLOGY

Three days after an intraperitoneal boost the spleens of the appropriate immune mice were removed and fused with the non-secretor myeloma cell Sp2/O. Spleen cell suspensions were prepared in serumless DMEM-high glucose medium and mixed with myeloma cells at a ratio of 4:1. This cell mixture was centrifuged at 1200 g for 10 minutes at room temperature. After removal of the supernatant, the cells were resuspended by gently tapping the tube. The fusion procedure was initiated by adding 1.0 ml of 45% w/v polyethylene glycol 3350 (Baker) at 37 degrees over a 30 seconds period.

The cells were occasionally mixed with a pipette tip for 90 seconds and 5 ml of serumless DMEM-high glucose medium was added over a 3 minute period. This was followed by the addition of 14 ml of DMEM-high glucose supplemented with 10% fetal calf serum, L-glutamine, hypoxanthine, aminopterin and thymidine (referred to as HAT medium). The HAT medium was added over a 1 minute period.

Appropriate volumes of HAT medium were added to cells and then the cells were centrifuged at 800×g for 7 minutes at room temperature. Supernatants were aspirated and the cell pellet disrupted with 10 ml of HAT medium. Peritoneal cells from Balb/c×C67BL/6 were added and the final volume adjusted so that two hundred thousand spleen cells were dispensed to each well. Approximately 14 days later tissue culture supernatants from wells containing hybridoma colonies were tested by ELISA for the desired reactivity with peptides conjugated to carrier proteins.

SCREENING PROCEDURES AND ELISA PROTOCOL

For screening purposes peptide 1 was conjugated to the BTG carrier protein and peptide 2 was coupled to the KLH carrier protein. The rationale for coupling peptides to different carrier proteins for immunization and screening was to avoid selecting antibodies reactive with the carrier protein. In the case of mice immunized with peptide 1 (Asp-KLH) the resulting hybridoma culture fluids were screened on peptides 1, 2 and 3 coupled to BTG. Prior to screening hybridoma supernatants, 500 ng of the peptide-carrier conjugate was dispensed to 96 well microtiter plates for overnight incubation at 37 degrees. After incubation, plates were washed and unbound sites on the plate were blocked with bovine serum albumin (BSA).

At the time of screening hybridoma supernatants 50 microliters (μl) of fluid was added to wells containing the peptide-carrier conjugates. Fluids were allowed to incubate overnight at 4 degrees. Hybridoma supernatants were removed the next day and wells were washed with the BSA solution. Each well subsequently received 50 μl of goat anti-mouse IgG antibody conjugated to horseradish peroxidase (GAMHRP) diluted in BSA phosphate buffered saline (PBS). Wells were incubated for 60 minutes a 37 degrees. GAMHRP was removed after incubation and wells were washed three times with PBS-BSA mixtures. The presence of bound GAMHRP was determined by adding 50 μl of the substrate o-phenylene diamine (OPD) in phosphate buffer containing 0.15% hydrogen peroxide. HRP in combination with its substrate (OPD) results in a yellow colored product. Development of the yellow product was allowed to occur at room temperature for 15 minutes. The enzymatic reaction was terminated by the addition of 50 μl of 4.5M sulfuric acid. Measurement of the resultant reaction product was accomplished by determining optical density (OD) at 488 nm. Presence of yellow color in the wells indicated that antibodies of interest were present in the hybridoma supernatants. The more antibody present in the culture fluid the higher the optical density.

SPECIFICITY OF MONOCLONAL ANTIBODIES FOR PEPTIDES OF INTEREST

In the next series of experiments the Mabs were tested for specificity with peptides 1, 2 and 3 without coupling the peptide to carrier proteins. Table 1 summarizes ELISA results of testing several monoclonal antibodies for reactivity on peptides not coupled to carrier proteins. Results demonstrate that the antibodies raised against peptide 1 containing aspartic acid at position 13 were reactive only with peptide 1 and not with peptide 2 or peptide 3 containing valine at position 13 glycine at position 13. Results also demonstrate that antibodies raised to valine at position 13 were reactive only with those peptides and not with peptides 1 and 3 containing aspartic acid and glycine respectively at position 13.

TABLE 1

| Specificity of Monoclonal Antibodies for Peptides of Interest (Values Represent Optical Density) | | | |
|---|---|---|---|
| Hybrid | Peptide 1 | Peptide 2 | Peptide 3 |
| D753-13 | 1.8 | 0 | 0 |
| D765-13 | 1.2 | 0 | 0 |
| V647-13 | 0.0 | 2.4 | 0 |

REACTIVITY OF ANTI-PEPTIDE MABS FOR ACTIVATED RAS P21S

D753-13 and D765-13 were tested for their reactivity with normal and activated cellular p21 s. To do these experiments we selected a cell line containing an activated N ras gene with a position 13 substitution of aspartic acid for glycine. As a control cell line we selected a cell line with glycine at position 13. A western blot procedure was performed to determine whether Mabs raised against peptide 1 containing aspartic acid at position 13 were reactive with activated cellular p21 s.

Nonradioactive extracts of cells containing activated or normal p21 s were applied to a 12.5% polyacrylamide gel. Cellular proteins were separated according to molecular weight by running an electric current through the gel. After this electrophoresis procedure the proteins were electrophoretically transferred to nitrocellulose membranes. After blocking the membranes with PBS containing 5% BSA they were incubated for one hour with either an anti-p21 Mab designated ras 10 or ascites fluid containing antibody reactive with peptide 1. The purpose of this experiment was to see if the anti-peptide 1 Mab was reactive with the activated cellular protein having aspartic acid at position 13. After incubation with either ras 10 or the anti-peptide specific Mabs the membranes were washed three times with PBS-NP-40. Membranes were then incubated with an anti-mouse immunoglobulin coupled to HRP for 1 hour to detect the mouse antibodies. Membranes were then washed 3 times with PBS-NP-40 and incubated with 4-chloro-1-napthol substrate to complete the reaction.

Our results demonstrated that the Mabs raised against the peptide with aspartic acid at position 13 were reactive with the activated p21 containing aspartic acid at position 13 but not reactive with normal p21 or p21 activated by other amino acid substitutions. These results demonstrate that Mabs raised to single amino acid substitution could detect the whole activated protein.

I claim:

1. Monoclonal antibody which specifically binds to an epitope on oncogenic ras proteins which comprises valine at position 13, but does not bind an epitope of normal, nononcogenic ras protein comprising glycine at position 13.

2. A fragment of the antibody of claim 1 which immunologically binds an epitope on oncogenic ras proteins which comprises valine at position 13, but does not bind an epitope of normal, nononcogenic ras protein comprising glycine at position 13.

3. A hybridoma that secretes monoclonal antibody of claim 1.

4. A hybridoma having ATCC Accession Number HB 9634.

5. A monoclonal antibody produced by the hybridoma having ATCC Accession Number HB 9634.

6. A method of detecting primary or metastatic cancers or preneoplastic lesions in an animal comprising testing fluid or lysate from cells from the animal for the presence of an oncogenic ras protein comprising valine at position 13, said method comprising contacting the fluid or lysate with the monoclonal antibody of claim 1 and determining whether antibody binding has occurred.

* * * * *